United States Patent [19]

Holleman et al.

[11] Patent Number: 5,003,992
[45] Date of Patent: Apr. 2, 1991

[54] ATRAUMATIC SCREW-IN LEAD

[76] Inventors: Timothy W. Holleman, 13600 Yancy St. NE., Ham Lake, Minn. 55304; Phong D. Doan, 5598 Park Pl. Dr., Shoreview, Minn. 55126; Kenneth R. Brennen, 160 Talmadge Way, Fridley, Minn. 55432; John M. Swoyer, 12012 Unity St. N.W., Coon Rapids, Minn. 55433

[21] Appl. No.: 398,350

[22] Filed: Aug. 23, 1989

[51] Int. Cl.$^5$ .............................................. A61N 1/05
[52] U.S. Cl. .................................... 128/785; 128/642; 128/786
[58] Field of Search ............... 128/642, 783, 784, 785, 128/786, 802, 419 P

[56] References Cited

U.S. PATENT DOCUMENTS

| H356 | 11/1987 | Stokes et al. | 128/785 |
| 4,046,151 | 9/1977 | Rose | 128/404 |
| 4,146,036 | 3/1979 | Dutcher et al. | 128/418 |
| 4,209,019 | 6/1980 | Dutcher et al. | 128/419 P |
| 4,282,885 | 8/1981 | Bisping | 128/785 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,624,266 | 11/1986 | Kane | 128/419 P |
| 4,649,938 | 3/1987 | McArthur | 128/419 P |
| 4,711,251 | 12/1987 | Stokes | 128/784 |
| 4,819,661 | 4/1989 | Heil, Jr. et al. | 128/786 |

FOREIGN PATENT DOCUMENTS 3300050  7/1984  Fed. Rep. of Germany .

Primary Examiner—Lee S. Cohen
Assistant Examiner—Scott M. Getzow

[57] ABSTRACT

An electrical stimulation lead incorporating an electrode assembly which dispenses a drug adjacent the stimulation site. The lead is provided with a fixation helix located at the distal end of the lead. An electrode may be extended distally within the helix. When extended, the electrode serves as a guard against perforation or other damage to tissue by the helix. In its retracted position, the electrode is located roughly adjacent the distal end of the lead body, and lies against the tissue to be stimulated. Advancing and retraction of the electrode is accomplished by means of a stylet which is removably engageable with the proximal end of the electrode. In one embodiment, the stylet functions to both advance and retract the electrode. In an alternative embodiment, the stylet is used only to advance the electrode, and retraction of the electrode is accomplished by a resilient conductor.

11 Claims, 2 Drawing Sheets

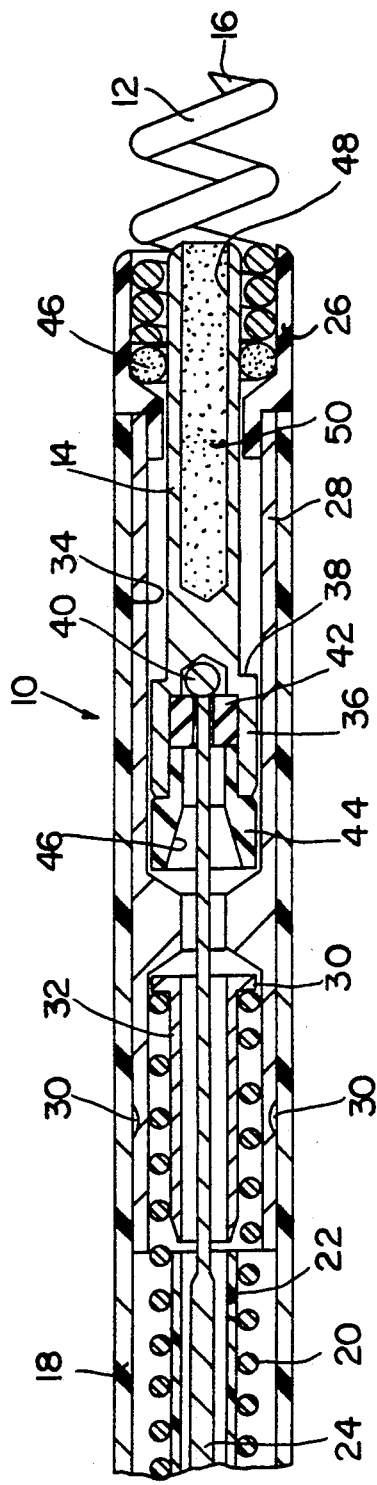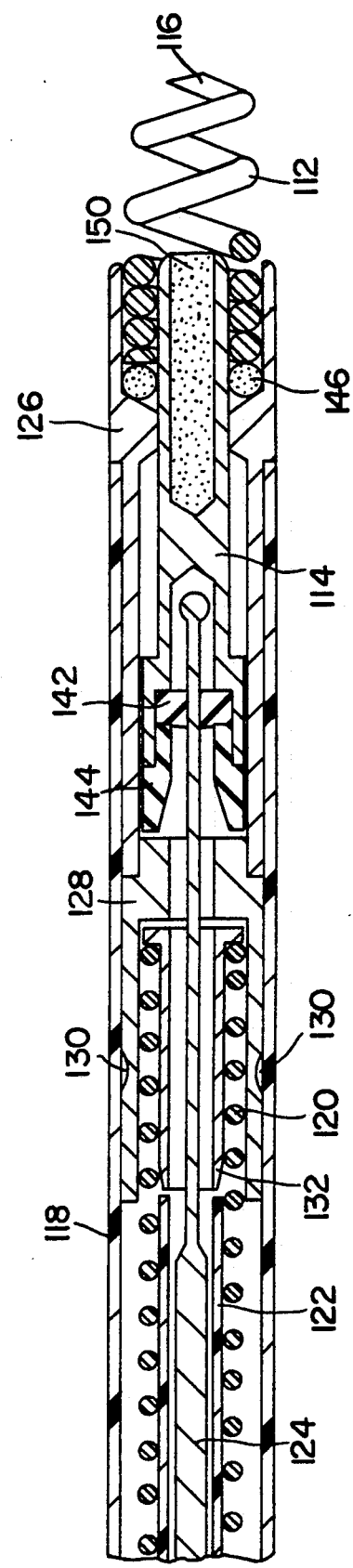

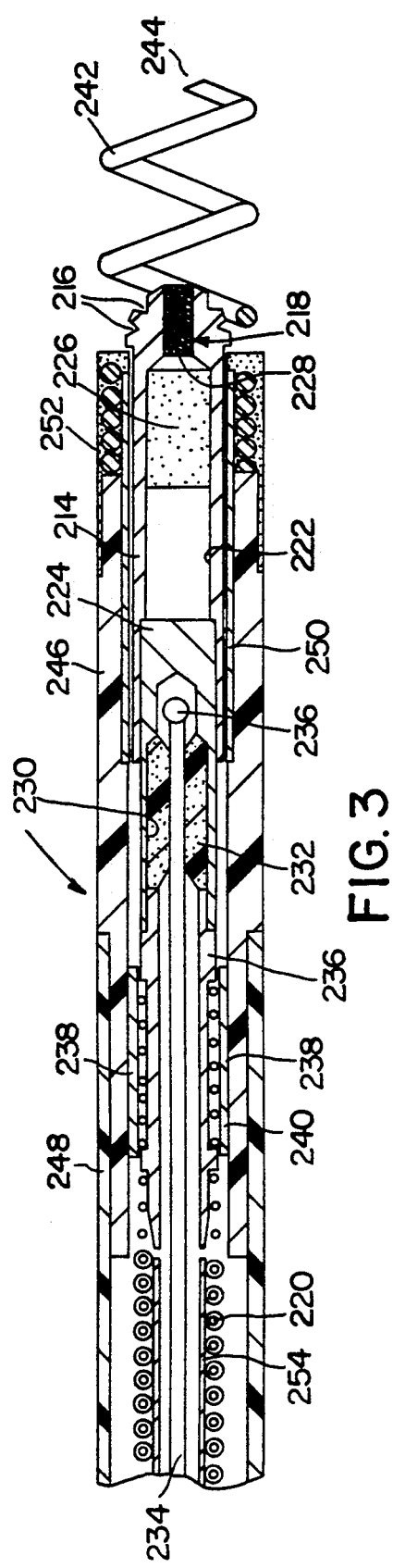
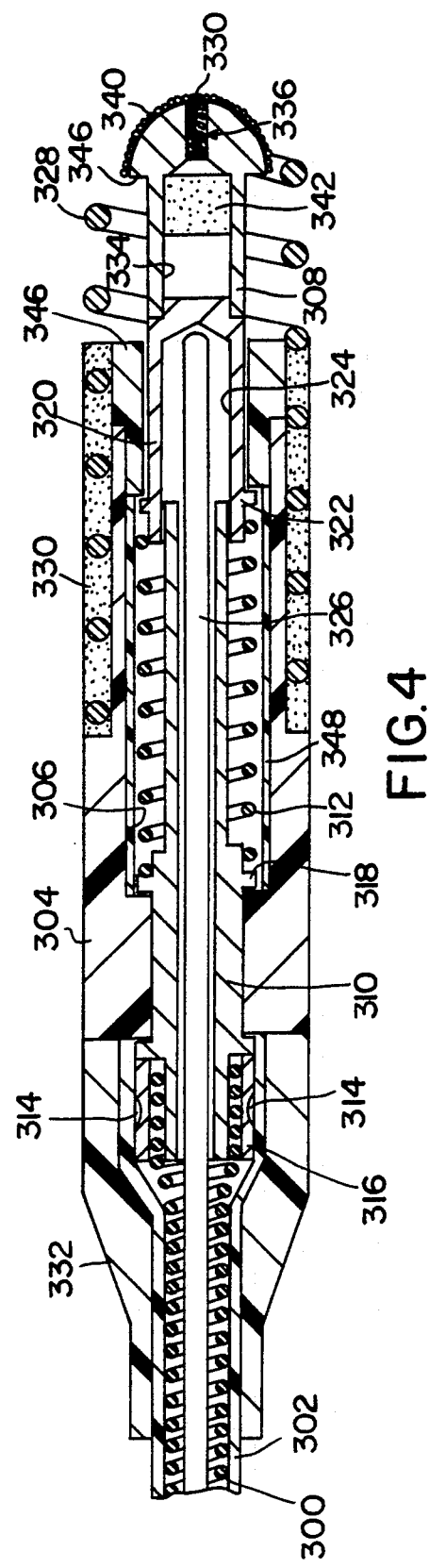
FIG. 3
FIG. 4

ATRAUMATIC SCREW-IN LEAD

BACKGROUND OF THE INVENTION

The present invention relates generally to electrical medical leads, and more particularly to stimulation leads of the type which dispense a steroid or other drug adjacent the stimulation site. The invention is particularly useful in the context of a cardiac pacing lead.

Delivery of a drug at the stimulation site of an implantable pacing lead is disclosed in U.S. Pat. No. 4,711,251, for a "Body Implantable Lead", issued to Stokes on Dec. 8, 1987, and incorporated herein by reference in its entirety. A particularly desirable configuration for such a lead is disclosed in U.S. Pat. No. 4,506,680, for a "Drug Dispensing Body Implantable Lead", issued to Stokes on Mar. 25, 1985, also incorporated herein by reference in its entirety. In this configuration, the drug to be dispensed is a steroid compounded with silicone rubber based medical adhesive to form a monolithic controlled release device (MCRD). The MCRD is located in a chamber within the stimulation electrode, and elutes out of the electrode through a porous elution path. The steroid acts as an antiinflammatory agent, reducing the adverse reaction of the tissue to the stimulation electrode.

Alternative embodiments of stimulation electrodes which elute a steroid or other drug are disclosed in U.S. Pat. No. 4,606,118, issued to Cannon et al and in U.S. Pat. No. 4,577,642, issued to Stokes. A myocardial pacing lead adapted to deliver steroid at the stimulation site is disclosed in Statutory Invention Registration No. H356. In this lead, a steroid is delivered through a barbed electrode to a delivery point within the myocardium.

Use of a fixation helix to attach a pacing or other stimulation electrode to tissue to be stimulated is disclosed in U.S. Pat. No. 4,046,151, issued to Rose. In this lead, the fixation helix is fixed with respect to the lead body and acts as the stimulation electrode. The fixation helix is shielded by a collapsible sheath which surrounds the helix until it is screwed into the tissue to be stimulated. An alternative design employing a fixation helix which functions as an electrode is disclosed in U.S. Pat. No. 4,282,885 issued to Bisping. In this lead, a plug or plunger is located within the helix, extending past the sharpened distal end of the helix. After the lead reaches the stimulation site, the plunger may be pulled into the distal end of the lead, allowing the electrode to be screwed into the tissue. The plunger is retracted by means of a stylet or wire which appears to be permanently affixed thereto.

An endocardial pacing lead in which the fixation helix is not used as an electrode is disclosed in U.S. Pat. No. 4,146,036 issued to Dutcher et al. In this lead, a separate electrode is provided at the distal end of the lead body. The fixation helix is shielded during introduction and passage to the stimulation site by means of a plunger slidably located within the helix. The plunger is advanced by means of a removable stylet. The lead is provided with a resilient plastic member which automatically retracts the plunger when the stylet is removed.

Yet another endocardial pacing lead employing a fixation helix is disclosed in German Patent Application No. 330,050 by Botvidsson et al. In this lead, a stylet is used to advance the electrode past the distal end of the helix to prevent damage due to the helix during passage of the lead to the stimulation site. Retraction of the electrode into the distal end of the lead body to expose the helix is accomplished by means of a resilient elastic member, similar to the mechanism for retracting the plunger described in the above-referenced Dutcher et al patent.

SUMMARY OF THE INVENTION

The present invention provides an endocardial pacing lead having a fixed screw, and including a monolithic controlled release device for elution of steroid in the vicinity of the fixation screw. This is particularly beneficial in overcoming the tendency of the heart to encapsulate the fixation screw with fibrotic tissue, reducing the efficiency of delivery of the stimulation pulse by the electrode. The controlled release device is located within a moveable plunger located within the fixation helix. In most embodiments of the invention, the plunger also serves as the stimulation electrode. When extended, the electrode or plunger prevents the helix from perforating or otherwise damaging the body tissue of the patient in which it is to be implanted. This is particularly important when passing the lead through the venous system and through the tricuspid valve. In its extended state, the electrode may also be used for determining sensing and pacing thresholds at various locations within the heart. When retracted, the electrode is located roughly adjacent the distal end of the pacing lead body. In use, the fixation helix is screwed into the tissue to be stimulated, holding the distal end of the pacing lead and the electrode adjacent the tissue. The plunger or electrode is configured such that steroid is eluted out of the distal end of the electrode, directly into contact with the tissue in the vicinity of the fixation helix.

In some embodiments, advancement and retraction of the plunger or electrode is accomplished by means of a stylet which is engaged within a socket in the proximal end of the slidable electrode. The socket is provided with means for releaseably engaging the end of the stylet. The stylet is engaged with sufficient firmness that the stylet may be used to retract the electrode, while still allowing the stylet to be disengaged from the proximal end of the electrode and withdrawn from the lead after retraction.

An alternative embodiment employs an electrode which is advanced by means of a stylet, but which is automatically retracted by means of a coil spring conductor located within the distal end of the electrode. In this embodiment, the coiled, spring conductor functions both to assure a reliable electrical connection to the electrode and to retract it within the housing, the electrode being fully retracted when the spring conductor is relaxed.

BRIEF DESCRIPTION OF THE DRAWINGS

FIG. 1 shows a side, cutaway view of a first embodiment of a pacing lead according to the present invention.

FIG. 2 shows a side, cutaway view of a second embodiment of a pacing lead according to the present invention.

FIG. 3 shows a side, cutaway view of a third embodiment of a pacing lead according to the present invention.

FIG. 4 is a side, cutaway view of a fourth embodiment of a pacing lead according to the present invention.

DETAILED DESCRIPTION OF THE INVENTION

FIG. 1 shows a side, cutaway view of the distal end of a pacing lead according to the present invention. The lead carries an electrode assembly 10 at its distal end. The electrode assembly includes a fixation helix 12 which is insulated from the electrode 14. Fixation helix 12 is provided with a sharpened distal tip 16 which is used to penetrate the tissue to which the lead is attached.

The lead is provided with an elongated insulative sheath 18 which extends to an electrical connector assembly located at the proximal end of the lead. The electrical connector assembly may be fabricated using any conventional connector structure, such as that disclosed in U.S. Pat. No. 4,258,725, issued Mar. 31, 1981, to O'Neill for a "Pacing Lead With Stylet And Tapered Terminal Pin", incorporated herein by reference in its entirety. Located within sheath 18 is an elongated, coiled conductor 20 which may be fabricated of MP35N alloy or other implantable biocompatible metal. A Teflon ® plastic sheath 22 is located within coiled conductor 20 and facilitates the passage of stylet 24.

The fixed portion of electrode assembly 10 may be referred to for convenience as the "electrode head". In this configuration, the electrode head includes a non-conductive head member 26, and a conductive head member 28. Conductive head member 28 may be fabricated of platinum alloy, stainless steel, MP35N alloy, elgiloy or other implantable metal. Non-conductive head member 26 may be fabricated of polyurethane or other rigid implantable plastic. Together head members 26 and 28 define a cylindrical lumen 34 in which electrode 14 is slidably mounted. Conductor 20 is coupled to head member 28 by means of crimps 30 which compress conductor 20 between head member 28 and crimping core 32.

Electrode 14 is slidably mounted within the lumen 34 of head member 28, and includes an expanded diameter portion 36 which frictionally engages the inner surface of lumen 34 to provide electrical continuity between metal head member 28 and electrode 14. The expanded diameter portion 36 of electrode 14 includes a forward facing shoulder 38 which engages the proximal end of non-conductive head member 26 to limit the movement of electrode 14 distally. When the distal facing shoulder 38 of electrode 14 is adjacent the proximal end of head member 26, the distal end of electrode 14 extends beyond the sharpened tip 16 of helix 12.

Electrode 14 is advanced and retracted by means of stylet 24, which is provided with an expanded diameter portion 40 at its distal end. As illustrated, expanded diameter portion 40 is ball shaped. Other configurations are also believed workable in conjunction with the invention. However, the ball tipped stylet configuration has substantial advantages when used in conjunction with pacing leads generally, and is believed to be the preferred embodiment of a stylet for use in the present invention. The ball tipped stylet is disclosed in detail in U.S. Pat. No. 4,498,482, issued to Williams et al for a "Transvenous Pacing Lead Having Improved Stylet" on Feb. 12, 1985.

Mounted within the recess at the proximal end of electrode 14 is a resilient ring 42, which engages stylet 24 proximal to the ball tip 40. Retainer ring 42 has an internal lumen of smaller diameter than ball tip stylet 40, allowing the stylet to be used to pull electrode 14 proximally, into the lumen 34 of conductive head member 28. Ring 42 may be made of silicone rubber or other elastomer or elastoplastic. In order for the present invention to function properly, it is necessary that ring 42 be sufficiently resilient to allow for the removal of stylet 40 with a nominal amount of force to avoid displacement of electrode head 10 during removal. Also located within the recess in the proximal portion of electrode 14 is a retainer 44, which retains ring 42 within electrode 14 and includes a conically tapered recess 46 to guide the tip of stylet 24 into ring 42. Retainer 44 is preferably fabricated of a rigid, biocompatible plastic such as a polyurethane.

At the distal end of the electrode head assembly 10, helix 12 is maintained within non-conductive head member 26 by means of adhesive, compression or other appropriate mechanical connection. As illustrated, helix 12 is spaced from electrode 14 and insulated from it by plastic head member 26. Also located within plastic head member 26 is a sealing ring 46 which frictionally engages the outer surface of electrode 14. Sealing ring 46 serves both to prevent entry of body fluids into the electrode assembly and to mechanically stabilize electrode 14 within lumen 34. It is necessary that the frictional resistance to movement of electrode 14 imparted by sealing ring 46 must be less than the force required to remove stylet 24 from ring 42 so that proximal movement of said electrode 14 may be accomplished using stylet 24.

Electrode 14 contains a monolithic controlled release device 50 impregnated with a drug for elution at the stimulation site. MCRD 50 may take the form of a plug of polymer incorporating the drug to be delivered, such as disclosed in U.S. patent application Ser. No. 07-398,228 by DiDomenico et al, for a "Medical Electrode Lead With Polymeric Monolithic Controlled Release Device", filed as of the date of this application, and incorporated by reference herein in its entirety. Alternatively, it may take the form of a porous, sintered structure containing the desired drug, or any of the various configurations illustrated in the above cited U.S. Pat. Nos. 4,711,251 or 4,506,680, issued to Stokes.

In use, the lead is advanced through the venous system with electrode 14 extended distally such that its distal end extends beyond the sharpened point 16 of helix 12. After the lead is passed through the tricuspid valve and into the ventricle, a suitable location for implant may be determined by placing the tip of electrode 14 adjacent heart tissue and taking stimulation and sensing thresholds. After a suitable location has been determined, stylet 24 is moved proximally to pull electrode 14 into recess 34 of conductive head member 28. The lead is then rotated around stylet 24 to screw helix 12 into the tissue at the desired stimulation site. After the lead has been firmly affixed to the tissue, stylet 24 is pulled proximally and removed from the lead.

FIG. 2 illustrates an alternate embodiment of a pacing lead according to the present invention. In general, the lead of FIG. 2 corresponds to the lead of FIG. 1 with the exception that the electrode head member is entirely metallic, allowing the fixation helix and head member to function as an electrode in addition to or as an alternative to the plunger electrode.

In FIG. 2, physical components corresponding to the components of the lead of FIG. 1 are labeled with corresponding numbers, e.g. helix 12 (FIG. 1), helix 112 (FIG. 2). Their functions and structures are generally the same as correspondingly numbered components in FIG. 1. Only components having differing structure and/or functions are discussed in detail below.

In the lead of FIG. 2, the electrode head includes a proximal head member 128 and a distal head member 126, both of which are fabricated of a biocompatible metal, such as platinum, MP35N alloy, or elgiloy. Head members 126 and 128 are preferably coupled to one another by means of a circumferential laser weld at their junction. Helix 112 is mounted within the distal end of head member 126, and is electrically and mechanically coupled thereto. As such, a continuous electrical path is provided from conductor 120 through proximal head member 128, to distal head member 126, and thereby to helix 112, allowing both the head member 126 and helix 112 to function as stimulating electrodes, if desired. Plunger 114 may be fabricated of a conductive implantable metal and function identically to electrode 14 discussed in FIG. 1. Alternatively, plunger 114 may be fabricated of a non-conductive material, such as a biocompatible plastic. In this case, plunger 114 would perform all the functions of electrode 14 (FIG. 1) except for stimulation of and/or sensing of electrical activity within the heart.

FIG. 3 shows the distal end of a third embodiment of a pacing lead according to the present invention. In this embodiment, there is a rigid mechanical and electrical connection between the extendable electrode 214 and conductor 220. Movement of the electrode 214 is allowed for by the inherent elasticity of the coiled conductor 220. This embodiment thus illustrates an alternative to the use of a conductive head member which frictionally or otherwise engages a sliding metal electrode located therein. The lead of FIG. 3 accomplishes the interconnection of the conductor 220 and the slidable electrode 214 solely by means of welding, crimping, swaging or other methods of rigid, mechanical interconnection.

In this embodiment, the electrode 214 is provided with two circumferential grooves 216 and a longitudinal bore 218. Externally, the distal end of electrode 214 displays the same configuration as the electrode illustrated in U.S. Pat. No. 4,502,492 issued to Bornzin, incorporated herein by reference in its entirety. In some cases, it may be desirable to coat the exterior of electrode 214 with platinum black, as described in the above-cited Bornzin patent. In this case, it is preferable that electrode 214 itself be fabricated of platinum or platinum alloy.

Electrode 214 includes an interior chamber 222, which is sealed at its distal end by means of a plug 224. Located within chamber 222 is a monolithic controlled release device 226, which contains a steroid or other drug adapted to be delivered to the distal end of electrode 214, by way of a sintered elution path 228. As illustrated, it is assumed that MCRD 226 is of the type which imbibes water in use, as described in the above-cited U.S. Pat. No. 4,506,680. Therefore, chamber 222 is sized to allow for substantial expansion of MCRD 226 as it imbibes body fluid.

Plug member 224 is provided with a lumen 230 open to its proximal end. Mounted within lumen 230 is a stylet retainer 232, which is preferably fabricated of a resilient material. Like the stylet retainers described in conjunction with the leads of FIGS. 1 and 2, above, the function of stylet retainer 232 is to releasably engage stylet 234, so that stylet 234 can pull electrode 214 proximally. Stylet 234 is provided with an expanded diameter portion 236, which may take the form of a ball-tip.

Mounted to the proximal end of plug member 224 is a crimping core 236. Crimping core 236 may be laser welded or mechanically attached to the proximal end of plug member 224. Conductor coil 220 is coupled electrically and mechanically to crimping core 236 by means of crimps 238, which frictionally hold conductor 220 between crimping core 236 and crimping sleeve 240.

In operation, stylet 236 is advanced distally to move electrode 214 distally through the interior of helix 242, until it extends beyond the distal end 244 of helix 242. Prior to inserting helix 242 into body tissue, electrode 214 is moved proximally by means of stylet 236, which also serves to maintain the distal end of the lead in an appropriate location. Helix 242 is screwed into body tissue by turning the entire lead body, allowing it to rotate around stylet 236. After helix 242 is screwed into the tissue allowing electrode 214 to contact the tissue, stylet 234 is pulled proximally, disengaging it from retainer 232.

In the embodiment illustrated, the electrode head 246 is fabricated of an insulative material, such as polyurethane, and adhesively coupled to the insulative outer sheath 248. Located within electrode head 246 is a metal sleeve 250, which serves as the mounting base for helix 242. Helix 242 may be attached to sleeve 250 by means of welding or mechanical attachment. Surrounding helix 242 in the area of attachment to the lead body is a biocompatible adhesive, which may be silicone rubber or polyurethane based.

As illustrated, fixation helix 242 is electrically active and is connected in parallel with electrode 214 by means of sleeve 250. However, in embodiments in which it is desired that the helix 242 be electrically isolated from electrode 214, sleeve 250 may be replaced with a non-conductive material, such as polyurethane or Teflon ®.

FIG. 4 shows a side sectional view through the distal end of a fourth embodiment of a pacing lead according to the present invention. This embodiment includes a plunger electrode which is spring loaded so that it will automatically retract into the distal end of the lead. The spring which serves to retract the electrode also serves as a direct, electrical connection between the electrode and the conductor of the lead, providing for rigid, mechanical interconnection of all electrically active components.

Like the leads illustrated in FIGS. 1-3, the lead of FIG. 4 is provided with an elongated coiled conductor 300, which is mounted within an elongated insulative lead body 302. The electrode assembly, mounted at the distal end of insulative lead body 302, includes an electrode head member 304, which is fabricated of a non-conductive, biocompatible material such as polyurethane. Head member 304 is provided with an internal lumen 306, in which a plunger electrode 308 is mounted. Plunger electrode 308 is connected to conductor 302 by means of a generally cylindrical metal member 310 and a conductive spring 312. The proximal end of cylindrical member 310 is mechanically and electrically connected to conductor 300 by means of crimps 314 which hold conductor 300 between the proximal end of member 310 and a cylindrical crimping sleeve 316. Spring 312 is laser welded or otherwise mechanically joined to member 310 at a shoulder 318. Spring 312 is similarly welded or otherwise mechanically connected to plug member 320 at shoulder 322. Plug member 320 is welded to the proximal end of electrode 308, and is provided with an inner recess 324 which is adapted to engage stylet 326. As such, in the lead as illustrated, there is an electrical path lead from conductor 300 to electrode 308, in which all interconnections are rigid, mechanical interconnections. This is believed to have some advantages over electrical interconnections employing members which may move relative to one another, relying on frictional engagement to provide the necessary electrical interconnections between the two mutually movable components.

A fixation helix 328 is mounted to the distal end of head member 304, and maintained in place by means of adhesive 330, which is preferably a urethane based adhesive such as a hot melt adhesive. Located at the proximal end of the electrode assembly is a strain relief sleeve 332, which provides a transition in flexibility between the electrode head 304 and the insulative lead body 302. Strain relief 332 being fabricated of silicone rubber or other appropriate elastic biocompatible plastic.

Electrode 308 is provided with an inner chamber 334, the distal end of which is sealed by plug member 324. The distal end of electrode 308 is provided with a longitudinal bore 336, which is filled with a porous, sintered elution path 338. A porous coating 340 is also applied to the exterior surface of electrode 308. This structure corresponds to that illustrated in the above cited U.S. Pat. No. 4,506,680, issued to Stokes, and functions in an identical fashion. An MCRD 342 is located within chamber 334 of electrode 308. In the configuration illustrated, MCRD 342 is water swellable, and thus occupies less than the complete volume of chamber 334. In use, drug elutes out of MCRD 342, through elution path 338, and into contact with the tissue adjacent the distal end of electrode 308.

In use, the lead is advanced through the venous system or otherwise to is desired location. While the lead is being advanced, stylet 326 is used to keep electrode 308 fully advanced out of the distal end of the lead, preventing damage due to helix 328. The distal movement of electrode 308 is limited by retainer 344, which engages with the front side of shoulder 322 of plug member 320. With the electrode 308 in the advanced position, stimulation and sensing thresholds can immediately be taken. After the electrode assembly is properly located, stylet 326 is moved proximally, allowing spring 312 to retract electrode 308 proximally, until the rearward facing shoulder 346 of electrode 308 rests adjacent retainer 344. The lead is then screwed into the tissue by rotation of the lead body around the stylet.

The above disclosure sets forth a variety of electrical stimulation leads provided with drug dispensing bodies located in plunger or electrodes, slidable within a fixation helix. In some embodiments, the fixation helix forms an electrode surface. In other embodiments, the fixation helix is electrically insulated from the electrode surface. Similarly, in some embodiments, the plunger containing the drug to be dispensed serves as an electrode, while in other embodiments the plunger is electrically inactive. While the mechanism for control of the plunger and the electrode structures displayed are set forth with some specificity in each of the four figures, these figures should be considered exemplary, rather than limiting with regard to the claims that follow, as the features displayed in each of the four drawings may be combined with one another in different combinations than specifically illustrated, and still fall within the scope of the invention claimed herein.

Similarly, all of the figures illustrate unipolar leads, bearing only a single electrode. However, the invention disclosed herein is believed equally valuable in the context of bipolar or multipolar leads.

In conjunction with the disclosure in the above specification, we claim:

1. A medical electrical lead comprising an elongated insulated conductor having a proximal end and a distal end, an electrical connector mounted to the proximal end of said conductor and an electrode head assembly mounted to the distal end of said conductor, said electrode head assembly comprising:

an electrode head member having a proximal end and a distal end and having a longitudinal lumen open to the distal end of said head member;

a fixation helix extending from the distal end of said head member, axially aligned with the lumen of said head member;

an electrode surface coupled to said conductor exposed to the exterior of said head member adjacent the distal end of said head member; and a plunger slideably mounted within the lumen of said head member, said plunger having a proximal end and a distal end and having means for dispensing a drug adjacent the distal end of said plunger, said plunger slideable between a first position in which said plunger extends through said fixation helix, the distal end of said plunger located distal to said fixation helix and a second position in which the distal end of said plunger lies adjacent the distal end of said head member, whereby when said fixation helix is screwed into body tissue to bring the distal end of said head member adjacent said body tissue, the distal end of said plunger and its associated means for dispensing a drug are located adjacent body tissue, when said plunger is located in said second position.

2. A lead according to claim wherein aid electrode surface comprises said fixation helix.

3. A lead according to claim 1 wherein said electrode surface comprises a portion of said head member.

4. A lead according to claim 1 or claim 2 or claim 3 further comprising means for moving said plunger between said first and second positions, said means comprising a stylet passing from the proximal end of said conductor to said plunger, and wherein said plunger comprises means for releasably receiving said stylet.

5. A lead according to claim 4 wherein said stylet comprises an expanded diameter portion adjacent its distal end and wherein said plunger comprises a recess located in its proximal end, said recess,.provided with resilient means for engaging said expanded diameter portion of said stylet, said resilient engaging means, in its relaxed condition, defining a central lumen therethrough having a diameter less than the diameter of said expanded diameter portion of said stylet.

6. A lead according to claim 5 wherein said resilient engaging means engages said expanded diameter portion of said stylet with a force greater than the frictional resistance to movement of said plunger within the lumen of said head member, whereby proximal movement of said stylet serves to retract said head member from said first position to said second position.

7. A lead according to claim 6 wherein said electrode head assembly further comprises a resilient sealing ring, frictionally engaging said plunger, and sealing said lumen in said head member from fluid ingress.

8. A medical electrical lead comprising: an elongated insulated conductor having a proximal end and a distal end, an electrical connector mounted to the proximal end of said conductor and an electrode head assembly mounted to the distal end of said conductor, said electrode head assembly comprising:

an electrode head member having a proximal end and a distal end and having a longitudinal lumen open to the distal end of said head member;

a fixation helix extending from the distal end of said head member;

a plunger electrode slideably mounted in said lumen of said head member, said plunger electrode having a proximal end and a distal end and having means for release of a drug adjacent the distal end of said plunger electrode, said plunger electrode slideable between a first location in which the distal end of said plunger electrode extends beyond said fixation helix and a second location in which the distal end of said plunger electrode lies adjacent the distal end of said head member, said plunger electrode further comprising a recess open to the proximal end of said head member;

a conductive, resilient member having a distal end fixedly mechanically and electrically mounted to the distal end of said plunger electrode and having a proximal end fixedly electrically and mechanically coupled to the distal end of said elongated conductor, said resilient member extendable from a first, relaxed position in which the distal end of said plunger electrode lies adjacent the distal end of said head member and a second, elongated configuration, when the distal end of said plunger electrode is extended to said first position.

9. A lead according to claim 8 wherein said fixation helix is electrical insulated from said plunger electrode.

10. A lead according to claim 9 wherein said recess in said proximal end of said plunger electrode extends for a distance at least equal to the distance over which said plunger electrode must be slid in order to move said plunger electrode from said first position to said second position and wherein said resilient member is coupled to said insulative conductor by means of a conductive, tubular member slideably located within said recess in said proximal end of said plunger electrode.

11. A lead according to claim 8 further comprising a stylet, passing down the length of said elongated conductor and having a distal end engaging with the recess in said proximal end of said plunger electrode.

* * * * *

UNITED STATES PATENT AND TRADEMARK OFFICE
CERTIFICATE OF CORRECTION

PATENT NO. : 5,003,992
DATED : April 2, 1991
INVENTOR(S) : Timothy W. Holleman, et al.

It is certified that error appears in the above-indentified patent and that said Letters Patent is hereby corrected as shown below:

Column 8, Line 39, after "claim", add --1--.

Column 8, Line 39, delete "aid", and insert in its place --said--.

Signed and Sealed this

Twentieth Day of September, 1994

Attest:

BRUCE LEHMAN

Attesting Officer      Commissioner of Patents and Trademarks